US00PP23666P3

(12) United States Plant Patent
Egger

(10) Patent No.: US PP23,666 P3
(45) Date of Patent: Jun. 11, 2013

(54) ***HEUCHERELLA* PLANT NAMED 'SUNRISE FALLS'**

(50) Latin Name: ***Heucherella* hybrid**
Varietal Denomination: Sunrise Falls

(75) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 82 days.

(21) Appl. No.: 13/200,475

(22) Filed: Sep. 22, 2011

(65) Prior Publication Data

US 2013/0081185 P1 Mar. 28, 2013

(51) Int. Cl.
*A01H 5/00* (2006.01)

(52) U.S. Cl.
USPC ..... Plt./441

(58) Field of Classification Search
USPC ..... Plt./441
See application file for complete search history.

*Primary Examiner* — June Hwu
(74) *Attorney, Agent, or Firm* — Klarquist Sparkman, LLP

(57) ABSTRACT

A new and distinct *Heucherella* plant substantially as shown and described, characterized by a vigorous, trailing habit, large, deeply lobed leaves, leaves yellow to lime green in spring and summer with red tones in fall and winter, a dark splatter pattern on the veins, and excellent vigor.

1 Drawing Sheet

Botanical denomination: *Heucherella* hybrid.
Variety designation: 'Sunrise Falls'.

BACKGROUND OF THE INVENTION

The present invention relates to a new and distinct cultivar of *Heucherella* and given the cultivar name of 'Sunrise Falls'. *Heucherella* is in the family Saxifragaceae. *Heucherella* 'Sunrise Falls' originated from a controlled cross between a proprietary unreleased seedlings *Heuchera* 217-4, as the seed parent, and *Tiarella* 42-5, as the pollen parent.

Compared to the seed parent *Heuchera* 217-4, the new cultivar is trailing rather than clumping.

Compared to *Tiarella* 42-5, the new cultivar has yellow to lime leaves rather than green.

Compared to *Heucherella* 'Yellowstone Falls', U.S. Plant Pat. No. 22,313, the new cultivar is larger, with leaves that are larger and more deeply lobed, and the leaves get red tones in the fall rather than staying yellow green.

SUMMARY OF THE INVENTION

This new *Heucherella* is unique in having the following characteristics:

1. a vigorous, trailing habit,
2. large, deeply lobed leaves,
3. leaves yellow to lime green in spring and summer with red tones in fall and winter
4. a dark splatter pattern on the veins, and
5. excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

FIG. 1 shows a 1 and a half year old greenhouse grown *Heucherella* 'Sunrise Falls' in a 10 inch container in flower in May in Canby, Oreg.

DETAILED PLANT DESCRIPTION

The following is a detailed description of the new *Heucherella* cultivar based on observations of one and a half-year-old specimens growing in 10" containers in the greenhouse in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on The Royal Horticultural Society Colour Chart, $5^{th}$ edition.

Plant:

*Form*.—Basal rosette and trailing, herbaceous perennial.
*Hardiness*.—USDA Zone 4 to 9.
*Size*.—16 cm tall from top of the foliage to the ground and 80 cm wide.
*Habit*.—Mounding and trailing.
*Vigor*.—Excellent.
*Roots*.—Fibrous, freely branching, fine, and white in color.

Stem:

*Size*.—Grows to 5 mm wide and 63 cm long.
*Internode length*.—0.5 to 2.3 cm.
*Stem color*.—Greyed Purple N186D.

Leaf:

*Type*.—Simple.
*Arrangement*.—Rosette and alternate.
*Shape*.—Broadly ovate.

*Lobing/division*.—5 palmate lobes with the terminal the longest, each with shallow secondary lobes; wide sinuses between terminal and secondary lobes.

*Venation*.—Palmate, topside Yellow Green 145C, bottom side 145D.

*Margins*.—Crenate.

*Apex*.—Mucronulate.

*Base*.—Cordate.

*Blade size*.—Grows to 13 cm long and 12 cm wide.

*Surface texture*.—Glandular both surfaces.

*Petiole description*.—Grows to 14 cm long and 2 mm wide, glandular hairs, closest to Greyed Purple 187B.

*Leaf color*.—Spring topside Yellow Green 145A with dark splatter pattern on the veins, Greyed Purple 187B (more yellow if grown outside); summer topside Yellow Green 144B with the pattern Greyed Purple 187A; bottom side spring and summer Yellow Green 146C with pattern Greyed Purple 187A; fall and winter leaves topside Greyed Red 181A with pattern Greyed Purple N187A, bottom side closest to Greyed Red 177D with pattern Greyed Purple N187B.

Inflorescence:

*Size*.—Grows to 5 cm wide and 22 cm long.

*Type*.—Raceme.

*Number of flowers per raceme*.—About 120.

*Number of racemes*.—About 20.

*Peduncle*.—Grows to 25 cm tall, 2 mm wide at base, glandular hairs, Brown 200D.

*Pedicel*.—Grows to 2 mm long, with glandular hairs, Yellow Green 146D tinted Greyed Red 181D.

*Bloom period*.—May to October in Canby, Oreg.

Flower bud:

*Size*.—2 mm wide and 4 mm long.

*Description*.—Glandular puberulent, ovoid.

*Color*.—White N155B.

Flower:

*Type*.—Perfect.

*Shape*.—Campanulate.

*Size*.—6 mm deep and 6 mm wide.

*Petal description*.—5 in number, oblanceolate, 4 mm long, tip acuminate, base attenuate, margin entire, glabrous and White NN155B on both sides.

*Calyx description*.—4 mm deep and 4 mm wide, with 5 lobes, divided ½ way to the base, campanulate, glandular hairs on both sides, tip acute, margin entire, light pink, White NN155B.

*Stamen description*.—5 in number, filaments 4 mm long, White NN155A, anthers sterile, less than 1 mm, White NN155A.

*Pistil description*.—One central two beaked pistil, 5 mm long, White NN155A.

*Fragrance*.—None.

*Lastingness*.—Each raceme blooms for about 2 weeks on the plant.

Fruit and seed: None.

Disease and pest tolerance: No known resistances. Excellent disease tolerance to powdery mildew. All *Heucherella* are susceptible to root weevils.

I claim:

1. A new and distinct *Heucherella* plant as herein illustrated and described.

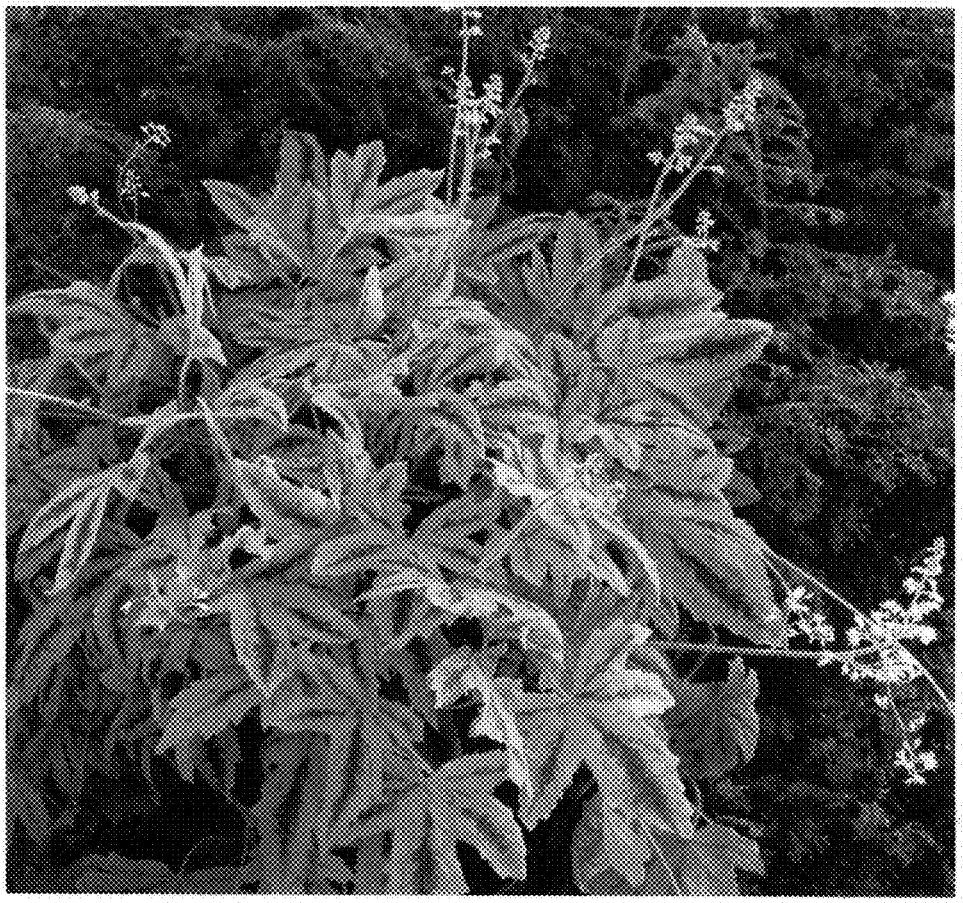

* * * * *